United States Patent [19]  [11]  4,152,444
Vischer et al.  [45]  May 1, 1979

[54] PHARMACEUTICAL COMPOUND PREPARATIONS WITH BACTERICIDAL ACTION

[75] Inventors: Wolfgang Vischer; Friedrich Kradolfer, both of Basel, Switzerland

[73] Assignee: Ciba-Geigy Corporation, Ardsley, N.Y.

[21] Appl. No.: 828,382

[22] Filed: Aug. 29, 1977

Related U.S. Application Data

[63] Continuation of Ser. No. 641,107, Dec. 15, 1975, abandoned, which is a continuation of Ser. No. 477,540, Jun. 7, 1974, abandoned, which is a continuation of Ser. No. 245,649, Apr. 19, 1972, abandoned.

[51] Int. Cl.$^2$ ............... A61K 31/415; A61K 31/445; A61K 31/40; A61K 31/34
[52] U.S. Cl. .............................. 424/273 R; 424/267; 421/274; 421/285
[58] Field of Search .............................. 424/285, 273

[56] References Cited

U.S. PATENT DOCUMENTS

3,751,567   8/1973   Konopka et al. .................. 424/114

OTHER PUBLICATIONS

The Merck Index, 8th ed., 1968, Merck & Co., Inc., Rahway, N. J., p. 738.

*Primary Examiner*—Jerome D. Goldberg
*Attorney, Agent, or Firm*—John J. Maitner

[57] ABSTRACT

The invention is directed to pharmaceutical and veterinary preparations having antibacterial action characterized by the contents of the following two bactericidally active substances
(1) a rifamycin compound
(2) a nitrofuran compound They show a synergistic enhancement of the bactericidal action as compared with the single antibactericidal components when given alone and they also suppress or prevent the development of resistance towards these antibiotics or antibacterial agents, especially towards rifampicin. Preferred ratios of the quantities of (1) and (2) contained in these preparations are 6:1 and 2:1. An especially suitable combination is rifampicin and nitrofurantoin. Other examples are the combination of 3-amino-rifamycin SV derivaties with known nitrofuran derivatives, such as nitrofurantoin, furzolidone or furaltadone.

9 Claims, No Drawings

PHARMACEUTICAL COMPOUND PREPARATIONS WITH BACTERICIDAL ACTION

CROSS-REFERENCE TO RELATED APPLICATIONS

This application is a continuation of application Ser. No. 641,107, filed Dec. 15, 1975 (now abandoned), which is a continuation of Ser. No. 477,540, filed June 7, 1974 (now abandoned), which is a continuation of application Ser. No. 245,649, filed Apr. 19, 1972 (now abandoned).

The present invention relates to new pharmaceutical and veterinary preparations, animal feeds or additives to animal feeds, which contain (1) bactericidally active rifamycin compound and
(2) a bactericidally active nitrofuran compound.

The new preparations according to the present invention exhibit a synergistic intensification of the bactericidal properties of the two components and are distinguished in particular by an inhibition of the build-up of resistance towards one or other of the components, in particular rifampicin, especially in the case of infections caused by Gram-negative bacteria. It is therefore possible to use them in human or veterinary medicine as excellent antibiotics for combating bacterial infections of the most diverse kinds, in particular those of which Gram-negative pathogens are the root cause, for example Escherichia coli, Proteus vulgaris, Shigella dysenteria, Salmonella typhi, Klebsiella pneumoniae.

In the form of animal feeds, the new preparations may be used for promoting growth.

Suitable bactericidially active rifamycin compounds are any compounds of the rifamycin group which are characterised by the cited action, such as rifamycin SV, rifamycin S, rifamycin B and their semi-synthetic derivatives and modification products, or their therapeutically useful salts. The following may be cited as examples of the semi-synthetic derivatives of the above mentioned basic substances of the rifamycin group:

(a) the amides of rifamycin B, for example the diethyl amide;

(b) the condensation products of rifamycin S or rifamycin O and aromatic O-diamines or O-aminophenols such as are described in U.S. Pat. No. 3,338,888;

(c) the adducts of amines of aliphatic character with rifamycin SV or their 25-desacetyl derivatives, as described in British Pat. Nos. 1,161,908 and 1,159,267 or in German Offenlegungsschrift No. 2039320, or in Experientia 1969, 1207;

(d) 3-formyl-rifamycin SV and the reaction products of this aldehyde with amines, hydroxylamine, substituted hydroxylamines or hydrazine or substituted hydrazines, as described in U.S. Pat. No. 3,342,810;

(e) the raction products of rifamycin O or rifamycin S with aromatic amines, for example aniline, as described in U.S. Pat. No. 3,542,765.

Numerous bactericidally active nitrofuran compounds according to (2) are known. They are derived preferably from 5-nitrofuran. Principally those nitrofuran compounds which are suitable for enteral, parenteral or, primarily, oral administration, are chosen for the pharmaceutical and veterinary preparations according to the present invention.

Particularly preferred are pharmaceutical or veterinary preparations of the cited kind which contain (1') a bactericidally active semi-synthetic derivative of rifamycin SV or rifamycin S selected from the group consisting of rifampicin, a 3-lower alkyl- or di-lower alkyl-amino-rifamycin SV or S, or a 3-morpholino-, 3-pyrrolidino-, 3-piperidino, 3-piperazino- or 3-lower cycloaklyamino-rifamycin SV or S which is unsubstituted in the 3-substituent or is substituted by lower alkyl groups, or a therapeutically useful salt thereof, and (2') a bactericidally active derivative of 5-nitrofuran or a therapeutically useful salt thereof.

A further combination of the above derivatives (1) and (2) which is likewise to be particularly highlighted results from the use of a 5-nitrofuran derivative according to (2') and a 3-morpholino-, 3-pyrrolidino-, 3-piperidino, 3-piperazino or 3-lower cycloalkylamino-rifamycin SV or S which is substituted in the 3-substituent at the carbon atoms by one or more hydroxyl groups and optionally also substituted by lower alkyl groups at the carbon atoms and/or at a further nitrogen atom which is optionally present.

From the group (1') there may be cited in particular:

3-dimethyl- and diethyl-amino-rifamycin SV, 3-isopropylamino rifamycin-SV, 3-morpholino-rifamycin SV, 3-pyrrolidino-rifamycin SV,
3-(3-methyl-pyrrolidino)-rifamycin SV, 3-(3,3-dimethylpyrrolidino)-rifamycin SV, 3-(3-methylpiperidino)-rifamycin SV, 3-(4-methyl-piperidino)-rifamycin SV, 3-(3,4-dimethylpiperidino)-rifamycin SV, 3-(4,4-dimethyl-piperidino-rifamycin SV, 3-(4-isopropyl-piperidino-rifamycin SV, 3-(3,3-dimethyl-piperidino)-rifamycin SV, 3-cyclopropylamino-rifamycin SV, 3-cyclohexylamino-rifamycin SV, 3-(N'-methylpiperazino)-rifamycin SV and their corresponding quinoid rifamycin S derivatives. Further suitable rifamycin SV or rifamycin S derivatives within the scope of the preferred derivatives cited above are 3-(3-hydroxy- or 4-hydroxypiperidino)-rifamycin SV or S.

Rifampicin is 3-(4-methyl-piperazinyl)-imino-methyl-rifamycin SV.

Bactericidally active nitrofurans mentioned under (2) are e.g. derivatives of 5-nitro-furfural, in particular the functional aldehyde derivatives thereof, such as acetals, for example lower alkyl or lower alkylene acetals, Schiff bases, hydrazones, for example guanyl hydrazones, semicarbazones, thiosemicarbazones or the reaction products of the aldehyde with ureas, carbamic acids or guanidines or compounds which are formed by condensation of the aldehyde group of the 5-nitrofurfural with a compound having an activated methyl or methylene group, for example a ketone, aldehyde, or thioketone, or with a carbocyclic or heterocyclic aromatic compound which is substituted by methyl groups, and which correspond to the general formula

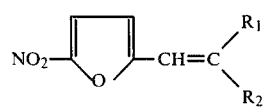

wherein $R_1$ represents hydrogen or a hydrocarbon radical, for example an alkyl or phenyl radical, and $R_2$ represents a carboxylic acid or thiocarboxylic acid radical or the radical of a carbocyclic or heterocyclic aromatic compound. The acyl radicals of a carboxylic acid or thiocarboxylic acid are, above all, lower alkanoyl or thioalkanoyl radicals or the acyl radicals of monocyclic lower aliphatic carboxylic acids, for example phenylacetic acid. The cited carbocyclic aromatic radicals are primarily unsubstituted or substituted phenyl radicals, the radicals of the cited heterocyclic aromatic compounds are in particular the radicals of pyridine, quinoline, pyrimidine, pyridazine, or triazines or of pyrazole or of derivatives of these compounds, in particular of compounds which are substituted by alkyl groups, chiefly methyl groups.

Suitable functional derivatives of 5-nitrofurfural are primarily: nitrofurantoin (trade-mark "Furadantin"), N-(5-nitro-2-furfurylidene)-amino-2-oxazolidinone (furazolidone) the dimethylaminoacetylhydrazone of 5-nitrofurfural, 1-dimethylaminoethyl-4-(5-nitrofurfurylidene-aminocarbamoyl)-5-amino-pyrazole, 5-methylcarbamoyl-oxymethyl-3-(5-nitrofurfurylidene-amino)-2-oxazolidinone or 5-propionyloxymethyl-3-(5-nitrofurfurylidene-amino)-2-oxazolidinone and 5-(morpholinomethyl-3-(5-nitrofurfurylidene-amino)-2-oxazolidinone (furaltadone). Of the condensation products of 5-nitrofurfurol with carbocyclic or heterocyclic aromatic compounds which carry active methyl groups, particular mention may be made of 3-dimethylamino-methylene-amino-6-[2-(5-nitro-2-furyl)-vinyl]-pyridazine.

Finally, nitrofuran derivatives are also suitable in which the 3-position of the furan ring is directly substituted by a heterocyclic radical, such as the 3-(5-nitro-2-furyl)-5-ureidomethyl-2-isoxazoline, the 1-methyl-3-(5-nitro-2-furyl)-1H-, pyrazolo-3,4-d-pyrimidine-4(5H)-one, the 4-cyano-5-ethoxymethylene-amino-1-methyl-3-(5-nitro-2-furyl)-pyrazole, the 5-amino-4-cyano-1-methyl-3-(5-nitro-2-furyl)-pyrazole, the 5-amino-4-cyano-1-(2-hydroxyethyl)-3-(5-nitro-2-furyl)-pyrazole, the 5-amino-4-carbamoyl-1-methyl-3-(5-nitro-2-furyl)-pyrazole or the 3-(5-nitro-furyl-2)-4-cyano-5-amino-isoxazole.

Especially important preparations according to the invention are those in which the bactericidally active rifamycin compound is selected from the above mentioned group (1') and the subsequently mentioned hydroxy-morpholino-, pyrrolidino, piperidino-, piperazino- or 3-lower cycloalkylaminorifamycin SV or S compounds, and the nitrofuran component is one of the above cited specific compounds.

The pharmaceutical preparations or animal feeds of the present application contain per dosage unit, for example a capsule or tablet, an effective or sub-effective dose of the rifamycin derivative under (1) and of the nitrofuran under (2) in any desired ratio, chiefly in a ratio between 10:1 and 0.1:1 and in particular between 6:1 and 1:1, and the conventional amounts of pharmaceutical carriers or extenders or diluents. By an effective dose is meant an amount of the antibiotic or bactericide in question which effects a bactericidal action when the antibiotic or bactericide is administered singly; a sub-effective dose is one which, in this mode of administration, produces no bactericidal effect.

The dosage unit of the new preparations contains the daily dose, or preferably proportional portions thereof, for example half the daily dose or a third of it. The dosage unit may also contain, however, a multiple daily dose. Preferably the dosage unit contains between 50 and 200 mg of the duran derivative and between 200 mg and 400 mg of the rifamycin derivative.

The pharmaceutical compound preparations according to the present application may be used for the same indications for which both components are also used. In particular, the new preparations are indicated for combating infections of the urinary and intestinal tracts. The daily dose of each individual component of the compound preparations according to the present application is preferably the same as in the case of treatment with the bactericide consisting of such component used alone.

Particular interest attaches to those preparations of the invention in which at least one of the components, for example the rifamycin component, is present in a dosage which is below that necessary for this component when used alone to achieve a satisfactory bactericidal effect, for example $\frac{1}{3}$ to $\frac{2}{3}$ of such dose.

Particularly important preparations are those which contain rifampicin as rifamycin component together with one of the specific nitrofuran derivatives cited hereinabove, primarily nitrofurantoin or furazolidone, for example a preparation for oral administration which contains 50 mg of nitrofurantoin and 300 mg of rifampicin in the dosage unit and this unit is used for a once daily application.

Both the rifamycin derivatives mentioned under (1) and the nitrofuran derivatives under (2) may be present in the new compound preparations according to the invention in the form of their salts. Suitable salts for the rifamycin derivatives are primarily alkali metal and ammonium salts and for the nitrogen derivatives, optionally acid addition salts and optionally also quaternary ammonium salts, in particular with esters of lower alkanols with hydrohalic acids, sulphuric acid or sulphonic acids. To manufacture the acid addition salts there are used above all acids which are suitable for forming therapeutically useful salts. As examples there may be cited: hydrohalic acids, sulphuric acids, phosphoric acids, nitric acid, perchloric acid; aliphatic, alicyclic, aromatic or heterocyclic carboxylic or sulphonic acids, e.g. formic, acetic, propionic, succinic, glycolic, lactic, malic, citric, ascorbic, maleic, hydroxymaleic or pyruvic acid; phenylacetic, benzoic, p-aminobenzoic, anthranilic, p-hydroxybenzoic, salicylic or p-aminosalicylic acid; embonic acid, methanesulphonic, ethanesulphonic, hydroxyethanesulphonic, ethylenesulphonic acid; halogenobenzenesulphonic, toluenesulphonic, naphthalenesulphonic acids or sulphanilic acid; methionine, tryptophane, lysine or arginine.

The pharmaceutical preparations of the present invention are preferably tablets or gelatin capsules comprising the active ingredients together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders; e.g. magnesium aluminium silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) adsorbents, colorants, flavors and sweeteners. Injectable compositions are preferably aqueous isotonic solutions or suspensions, and suppositories or ointments are advantageously fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 95%, preferably about 50 to 95%, of the active ingredients listed under (1) and (2).

The present invention also provides a method for suppressing or preventing resistance developed by microorganisms towards bactericidally active rifamycin compounds or bactericidally active nitrofuran compounds wherein there is administered a bactericidally active rifamycin compound along with a bactericidally active nitrofuran compound as hereinbefore described. These two bactericidal derivatives can be administered separately, for instance at different hours of the day or preferably together, for instance in the form of the pharmaceutical preparations as hereinbefore described. This process is especially useful in preventing or suppressing resistance caused by gram - negative bacteria, and especially in the case of resistance developed towards rifampicin.

The invention is illustrated by the following Examples.

EXAMPLE 1

Manufacture of 1000 capsules each weighing 380 mg and containing 350 mg of the active ingredients:

| Composition: | |
|---|---|
| rifampicin | 300 g |
| nitrofurantoin | 50 g |
| wheat starch | 20 g |
| magnesium stearate | 10 g |
| | 380 g |

Procedure

All powders are passed through a screen with an opening of 0.6 mm and mixed thoroughly. 0.5 ml hard gelatine capsules are filled with 380 mg of said mixture, using a capsule filling machine.

EXAMPLE 2

Manufacture of 1000 capsules each weighing 490 mg and containing 450 mg of the active ingredients:

| Composition: | |
|---|---|
| rifampicin | 300 g |
| nitrofurantoin | 150 g |
| wheat starch | 30 g |
| magnesium stearate | 10 g |
| | 490 g |

The manufacture is carried out as described in Example 1.

EXAMPLE 3

Manufacture of capsules proceeding analogously to Example 1, but using furazolidone instead of nitrofurantoin.

EXAMPLE 4

Manufacture of capsules proceeding analogously to Example 1, but using rifamycin PH, i.e. the condensation product of rifamycin S or O with o-phenylenediamine, in the form of the hydroquinone, instead of rifampicin and 3-(5-nitro-2-furyl)-5-ureidomethyl-2-isoxazoline (as hydrochloride) instead of nitrofurantoin.

EXAMPLE 5

Manufacture of capsules proceeding analogously to Example 2, but using 3-(5-nitro-2-furyl)-5-ureidomethyl-2-isoxazoline (as hydrochloride) as nitrofuran component instead of nitrofurantoin.

EXAMPLE 6

Manufacture of capsules proceeding analogously to Example 1, but using 25-desacetylrifampicin instead of rifampicin.

EXAMPLE 7

Manufacture of capsules containing rifampicin and 1-dimethylaminoethyl-4-(5-nitrofurfurylidene-aminocarbamoyl)-5-amino-pyrazole (as sulphate) as nitrofuran component instead of nitrofurantoin by proceeding analogously to Example 1.

EXAMPLE 8

Manufacture of 1000 capsules each weighing 122 mg and containing 116.5 mg of active ingredients:

| Composition: | |
|---|---|
| rifampicin | 100 g |
| nitrofurantoin | 16.5 g |
| wheat starch | 3.5 g |
| magnesium stearate | 2.0 g |
| | 122.0 g |

Preparation: as in Example 1.

EXAMPLE 9

Manufacture of 1000 capsules each weighing 163 mg and containing 150 mg of active ingredients:

| Composition: | |
|---|---|
| rifampicin | 100 g |
| 5-methyl-carbamoyl-oxymethyl-3-(5-nitro-furfurylidene-amino)-2-oxazolidinone | 50 g |
| maize starch | 10 g |
| magnesium stearate | 3 g |
| | 163 g |

Preparation: as in Example 1.

EXAMPLE 10

Manufacture of 1000 capsules each weighing 350 mg and containing 320 mg of active ingredients:

| Composition: | |
|---|---|
| rifampicin | 300 g |
| nitrofurantoin | 20 g |
| wheat starch | 20 g |
| magnesium stearate | 10 g |
| | 350 g |

Preparation: as in Example 1.

EXAMPLE 11

Manufacture of capsules by a procedure analogous to Example 1, but using 3-morpholino-rifamycin SV instead of rifampicin.

EXAMPLE 12

Manufacture of capsules by a procedure analogous to Example 2, but using 3-morpholino-rifamycin instead of rifampicin.

EXAMPLE 13

Manufacture of capsules by a procedure analogous to Example 1, but using 3-ethylamino-rifamycin SV instead of rifampicin.

EXAMPLE 14

Manufacture of capsules by a procedure analogous to Example 3 which contain 3-(N'-methyl-piperazino)-rifamycin SV instead of rifampicin and furaltadone instead of nitrofurantoin.

EXAMPLE 15

Manufacture of capsules by a procedure analogous to Example 1 which contain 3-hydroxypiperidino-rifamycin SV instead of rifampicin and furazolidone instead of nitrofurantoin.

EXAMPLE 16

Manufacture of capsules by a procedure analogous to Example 10 which contain 4-hydroxypiperidino-rifamycin SV instead of rifampicin.

EXAMPLE 17

Manufacture of capsules by a procedure analogous to Example 1 which contain 3-(N'-morpholino-iminomethyl)-rifamycin SV instead of rifampicin and 3-dimethylamino-methyleneamino-6-2-(5-nitro-2-furyl)-vinyl-pyridazine.

EXAMPLE 18

Manufacture of capsules by a procedure analogous to Example 2 which contain rifamycin SV instead of rifampicin.

EXAMPLE 19

Manufacture of capsules by a procedure analogous to Example 1 which contain rifamide instead of rifampicin and furazolidone instead of nitrofurantoin.

EXAMPLE 20

Manufacture of capsules by a procedure analogous to Example 2 which contain 3-(1',8',8'-trimethyl-3'-azabicyclo[3',2',1']oct-3'-yl)-rifamycin SV instead of rifampicin and furaltadone instead of nitrofurantoin.

We claim:

1. A method for treating bacterial infections in humans and animals which comprises administering to said human or animal an antibacterially effective amount of a preparation of (1) rifampicin and (2) nitrofurantoin wherein the two components (1) and (2) are present in a ratio of from 6:1 to 1:1.

2. A method of claim 1, wherein the preparation is orally administered.

3. A method of claim 1, wherein the preparation is parenterally administered.

4. A method of claim 1, wherein the preparation is administered in the form of gelatine capsules.

5. A pharmaceutical and veterinary preparation for treating bacterial infections comprising (1) refampicin and (2) nitrofurantoin wherein the two components (1) and (2) are present in a ratio of from 6:1 to 1:1.

6. The preparation of claim 5, which contains the two components (1) and (2) in a ratio of 6:1.

7. The preparation of claim 5, which contains the two components (1) and (2) in a ratio of 2:1.

8. The preparation of claim 5, which contains 50 mg of rifampicin in the dosage unit.

9. The preparation of claim 5, which contains 150 mg of nitrofurantoin and 300 mg of rifampicin in the dosage unit.

* * * * *